(12) United States Patent
Hettrick et al.

(10) Patent No.: US 8,478,400 B2
(45) Date of Patent: Jul. 2, 2013

(54) PRESSURE AND IMPEDANCE BASED DISCRIMINATION OF HEMODYNAMIC STABILITY

(75) Inventors: Douglas A. Hettrick, Andover, MN (US); Kevin P. Vincent, St. Louis, MO (US); Shantanu Sarkar, Roseville, MN (US); Yong Kyun Cho, Maple Grove, MN (US); Todd M. Zielinski, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1469 days.

(21) Appl. No.: 12/108,818

(22) Filed: Apr. 24, 2008

(65) Prior Publication Data
US 2009/0270934 A1 Oct. 29, 2009

(51) Int. Cl.
*A61N 1/39* (2006.01)
(52) U.S. Cl.
USPC .............................. 607/6; 600/508
(58) Field of Classification Search
USPC ....................... 600/506–508; 607/6
See application file for complete search history.

(56) References Cited

U.S. PATENT DOCUMENTS

| 5,168,869 | A  | * | 12/1992 | Chirife ........................... 607/25 |
| 7,286,875 | B1 |   | 10/2007 | Park et al. |
| 2005/0027323 | A1 |   | 2/2005 | Mulligan et al. |
| 2007/0149890 | A1 |   | 6/2007 | Li et al. |
| 2007/0191901 | A1 |   | 8/2007 | Schecter |
| 2009/0270933 | A1 | * | 10/2009 | Hettrick et al. .................. 607/6 |

OTHER PUBLICATIONS

Wood, MA, et al. "Comparison of right ventricular impedance, pulse pressure and maximal dP/dt for determination of hemodynamic stability of ventricular arrhythmias associated with coronary artery disease" Am J Cardiol 1990; 66:575-582.

* cited by examiner

*Primary Examiner* — Mark W Bockelman
(74) *Attorney, Agent, or Firm* — Michael C. Soldner

(57) ABSTRACT

An implantable cardioverter defibrillator evaluates the hemodynamic stability of an arrhythmia to determine whether or not to defibrillate. The device obtains cardiac pressure and cardiac impedance data and evaluates a phase relationship between these parameters. Hemodynamically stable rhythms will result in an out of phase relationship.

21 Claims, 9 Drawing Sheets

PRESSURE AND IMPEDANCE BASED DISCRIMINATION OF HEMODYNAMIC STABILITY

FIELD

This present disclosure generally relates to implantable medical devices and mores specifically to implantable medical devices that sense cardiac impedance and pressure.

BACKGROUND

Implantable medical devices (IMDs) provide a variety of monitoring, diagnostic, and therapy functions. For example, implantable pulse generators (IPGs) provide low power cardiac pacing and implantable cardioverter defibrillators (ICDs) provide high power defibrillation therapies (often in addition to pacing). These devices often monitor cardiac performance and provide targeted therapies based upon the data collected.

The performance of any given IMD is limited by the type of data collected. For example, most IMDs readily and accurately monitor heart rate. This parameter, while basic, provides invaluable information for cardiac devices. In many instances, this parameter alone provides sufficient information for the complete and proper operation of the device. IPGs may be set so as to deliver pacing whenever a patient's heart rate falls below a predetermined value (bradycardia). Often, the desired minimum value will be based on a secondary parameter, such as an activity level as sensed by an accelerometer. Thus, a desired target heart rate is set for a patient based upon a sensed activity level. If the patient's heart rate falls below this level, then the IPG provides a pacing therapy. As these values change and the patient's heart responds differently, the IPG preferably delivers therapy only when needed.

In the high power context, heart rate is also a core parameter. Ventricular tachycardia (VT) and ventricular fibrillation (VF) are potentially dangerous arrhythmias that generally correlate to heart rate. For example, VT would generally be classified for a rate of 150 to 250 beats per minute (bpm), while VF would be classified for rhythms greater than 250 bpm. Of course, during exercise, a patient's heart rate may fall within this prespecified VT range despite that rate being normal for the level of activity. Conversely, VF may occur at a lower rate and still be problematic. Thus, there is a desire to provide additional discrimination when detecting and categorizing VT/VF.

As VT/VF may be life threatening, discrimination protocols are set to err on the side of caution and provide therapy. False positives are problematic in that the high energy therapy may be physically uncomfortable and even painful to the patient. Furthermore, the therapy is often delivered without warning to the patient thereby taking them by surprise, even though the therapy is appropriately applied to a genuine arrhythmia. Therefore it is desirable to lower the frequency of both necessary and unnecessary shocks.

Many actual ventricular (or atrial) tachyarrhythmias spontaneously terminate after a very short duration. Since the hemodynamic status of the patient is unknown to the device at the time of therapy, most devices are programmed to deliver therapy as quickly as possible following detection. The time to therapy is generally limited by the time required to detect and confirm the arrhythmia as well as the time for the main defibrillation capacitors to charge. If hemodynamic parameter describing the stability of the arrhythmia were provided to the device, then an option would be available to delay therapy so that the arrhythmia might terminate spontaneously thereby avoiding the need to shock.

BRIEF SUMMARY

In one embodiment, an implantable medical device (IMD) is provided that includes a microprocessor configured to control operation of the IMD; a pressure sensor coupled with the microprocessor and configured to provide ventricular pressure data to the microprocessor; and an impedance sensor coupled with the microprocessor and configured to provide ventricular impedance data to the microprocessor, wherein the microprocessor is configured to determine hemodynamic stability based upon a phase relationship between the ventricular pressure data and the ventricular impedance data.

In another embodiment, the IMD further includes a therapy delivery module operably coupled with the microprocessor, wherein the microprocessor causes the therapy delivery module to deliver a therapy based upon the determination of hemodynamic stability.

In another embodiment, the microprocessor precludes the therapy deliver module from delivering a high power therapy if an arrhythmia is determined to be hemodynamically stable.

In another embodiment, an implantable medical device is provided that includes a microprocessor; a therapy delivery module operably coupled with the module and configured to selectively deliver a defibrillation waveform or a pacing therapy in response to a cardiac arrhythmia; a cardiac lead operably coupled with the microprocessor and the therapy delivery module and including one or more electrodes to provide the defibrillation waveform and the pacing therapy; an impedance sensor communicatively coupled with the microprocessor to deliver ventricular impedance data, wherein at least a portion of the impedance sensor includes at least one of the one or more electrodes to sense impedance; and a pressure sensor communicatively coupled with the microprocessor and configured to provide ventricular pressure data to the microprocessor, wherein the microprocessor is further configured to determine a phase relationship between the pressure data and the impedance data and to determine hemodynamic stability of a cardiac rhythm based upon the determined phase relationship.

In another embodiment, the microprocessor precludes the therapy delivery module from delivering the defibrillation waveform unless the cardiac rhythm is hemodynamically unstable.

In another embodiment, the microprocessor precludes the therapy delivery module from delivering the defibrillation waveform unless the cardiac rhythm is hemodynamically unstable or until a less aggressive therapy has proven unsuccessful if the cardiac rhythm is hemodynamically stable.

In yet another embodiment, an IMD is provided that includes means for sensing cardiac pressure; means for sensing cardiac impedance; and means for determining hemodynamic stability based upon a phase relationship between the sensed cardiac pressure and the sensed cardiac impedance.

Under normal hemodynamic conditions the left ventricular pressure is approximately 90 degrees out of phase from the ventricular volume wave form in the time domain. However, under conditions of hemodynamic instability, this phase relationship is lost and the phase relationship between the signals becomes random. Under such conditions, it is unlikely that the ventricle can function adequately to maintain circulation and adequate cardiovascular function. Therefore, monitoring the phase relationship between pressure and impedance provides a method to monitor hemodynamic instability during an arrhythmia.

DETAILED DESCRIPTION

The present disclosure provides embodiments of IMDs that increase the sensitivity and specificity of ventricular tachyarrhythmia event (VT/VF) detection by utilizing a combination of sensed ventricular pressure data and sensed impedance data to determine the hemodynamic stability of a rhythm. The hemodynamic stability in turn is utilized to determine which rhythms require aggressive therapy (i.e., high energy defibrillation) and which rhythms require less aggressive therapies (e.g., anti-tachy pacing (ATP)) or do not require therapy at all.

The IMD determines a phase relationship between ventricular pressure and cardiac impedance. The phase relationship provides an accurate and readily discernable indication of hemodynamic stability. During a normal cardiac contraction, the left ventricle (LV) fills with blood and expands in volume. During this time, LV pressure increases until reaching a maximum. Conversely, as the volume of blood in the LV increases, the measured impedance across this heart chamber decreases due to the conductivity of the blood. When the LV contracts it ejects a substantial portion of the blood volume thereby reducing the volume of blood in the chamber and lowering the LV pressure. With the lower blood volume, the measured impedance is higher. Thus, in a normal hemodynamically stable cardiac event cycle measured pressure and measured impedance will be out of phase with one another. While described with respect to LV values, it should be appreciated that other cardiac pressure and impedance values will vary in a similar fashion and may be utilized accordingly, as will be described herein.

Figure 1:
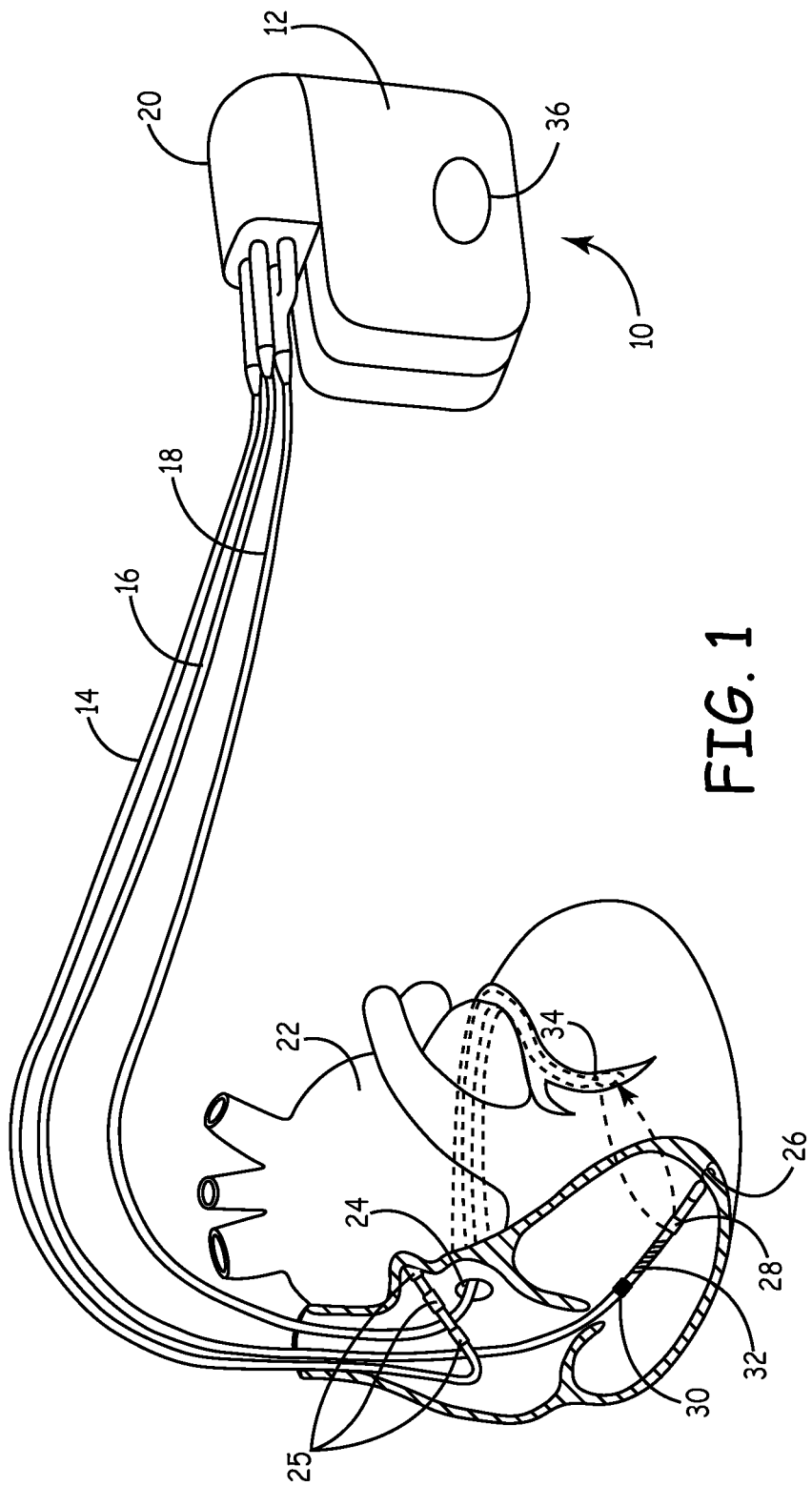
FIG. 1 is an isovolumetric illustration of an IMD having a plurality of leads extending into a partially section view of a human heart.

FIG. 1 illustrates an IMD 10 coupled with a heart 22 via a plurality of leads 14, 16, 18. The IMD 10 includes a housing or "can" 12 and a header portion 20. A right atrial (RA) lead 14 is coupled with the header 20 and includes one or more RA electrodes 25 disposed near a distal end and located within the right atrium of the heart 22. A right ventricular (RV) lead 16 is also coupled with the header 20. The RV lead 16 includes a tip electrode 26, a ring electrode 28, a pressure sensor 30 and a coil electrode 32. A left ventricular (LV) lead 18 includes a tip electrode 34. The LV lead 18 is coupled with the header 20 at its proximal end and is passed through the coronary sinus (CS) 24 and through a cardiac vein so that the electrode 34 is located proximate the left ventricle of the heart 22. The can 12 further includes a can electrode 30. It will be appreciated that the IMD 10 may be configured with different leads and/or with leads having different electrode configurations.

Figure 2:
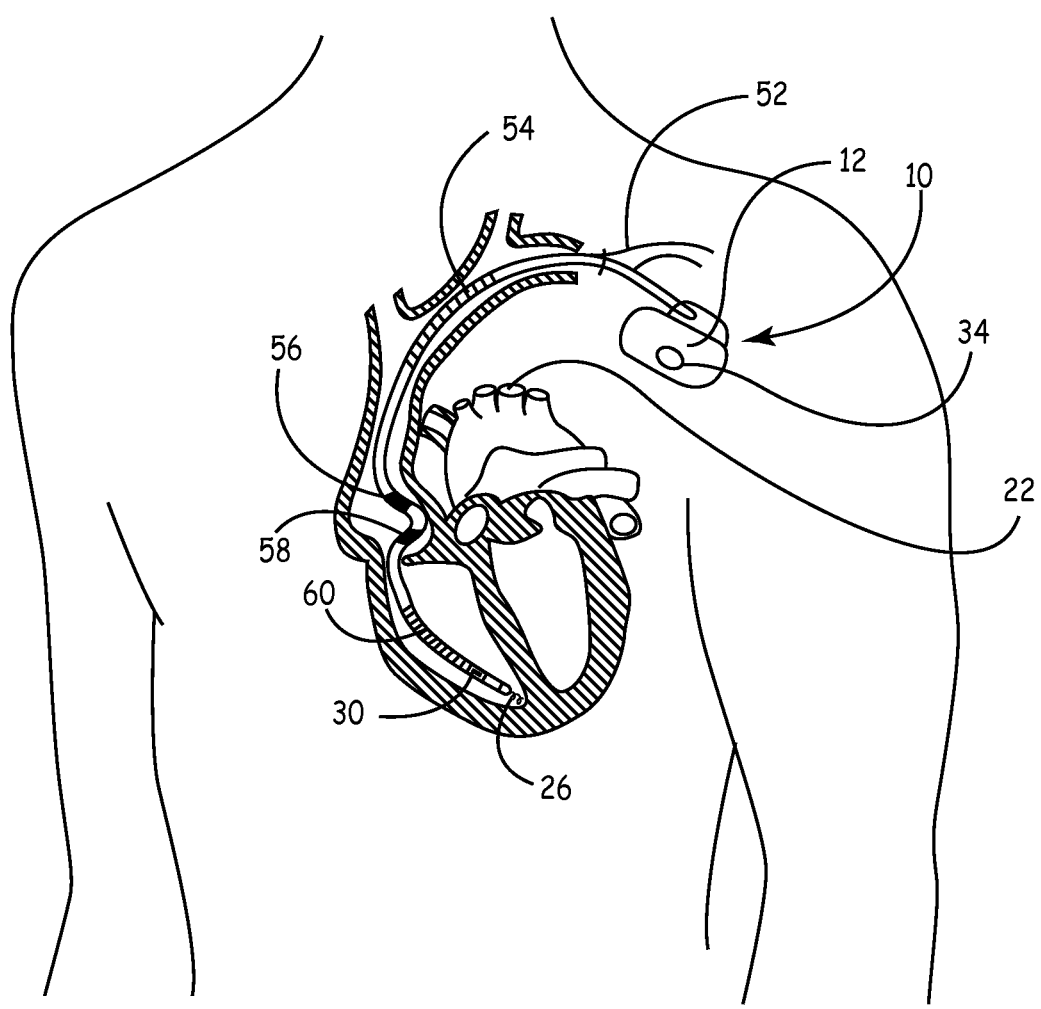
FIG. 2 illustrates an alternative embodiment of an IMD.

As an example, IMD 10 is illustrated in FIG. 2 having a single RV lead 52. Lead 52 has numerous electrodes and sensors disposed along its length and coupled with the can 12 via separate conductors. As illustrated, RV lead 52 includes a SVC coil 54, atrial electrodes 56, 58, RV coil electrode 60, RV pressure sensor 30, and RV tip electrode 26.

Figure 3:
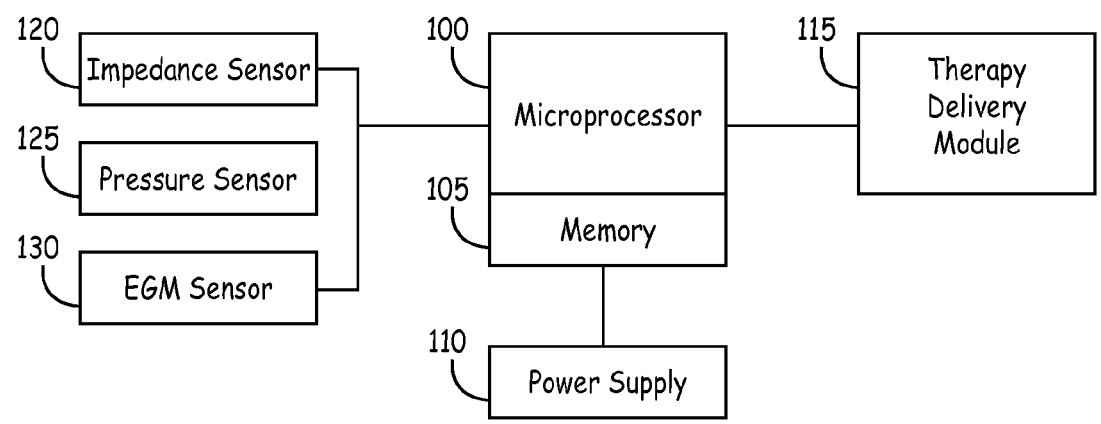
FIG. 3 is a block diagram illustrating functional components of an IMD.

The components and operation of the IMD 10, configured as an ICD are generally conventional and will not be described in detail. FIG. 3 is a block diagram illustrating some of these components. As illustrated, the IMD 10 includes a microprocessor 100 coupled with a battery or power supply 110. A memory 105 is provided and includes a portion dedicated to storing the operational algorithms and parameters for device function as used in combination with the microprocessor. In addition, and typically separate, a portion of writeable memory is provided to store data collected by the IMD 10. The microprocessor 100 controls operation of the therapy deliver module 115 based upon the stored algorithms, parameters and protocols, to deliver, for example, defibrillation waveforms when required. Alternative therapies, such as pacing, cardioversion, anti-tachy pacing, and the like may also be provided and delivered via therapy control module 115.

Numerous sensors may be included to provide data to the IMD 10. Three are illustrated herein. Namely, the IMD 10 includes an impedance sensor 120, a pressure sensor 135 and an EGM sensor 130. Any pairing of the electrodes illustrates in FIGS. 1 and 2 (as well as other known electrode types/positions) may be utilized to gather EGM data as well as impedance measurements. The pressure sensor 125 utilizes a pressure sensor disposed on, within or proximate the heart 22. As illustrated, the pressure sensor 125 utilizes a RV pressure sensor 30 disposed within the right ventricle. It should be appreciated the direct measurement of left ventricular (or arterial) pressure may be ideal, however placing such a sensor in the left ventricle is challenging. As will be described below, RV pressure data is sufficiently similar to LV pressure data to facilitate implementation. The impedance sensor 120 operates by driving current between a pair of electrodes and measuring the resulting signal, either with the same receiving electrode or by utilizing one or more electrodes other than the driving pair.

Impedance may be measured between one or more electrode pairs within a single heart chamber (e.g., the right ventricle). A constant current stimulation field is established between electrode pairs disposed within the ventricle. Impedance (or its inverse, conductance) is measured between adjacent electrode pairs and the value from each electrode pair is summed to derive an impedance/conductance signal that is proportional to the volume of the heart chamber measured. Specifically, $$V(t) = \frac{G(t)\rho l^2}{\alpha} + V_p$$

wherein, V is equal to the total heart chamber volume, G is equal to conductivity, $\rho$ is equal to the resistivity of blood, l is the interelectrode distance, and $V_p$ and $\alpha$ are correction factors accounting for current leakage out of the electrical field and non-homogeneity of the electrical field.

Alternatively, direct impedance measurements from an RV electrode (e.g., RV tip electrode 26) across the LV to e.g., the LV tip electrode 34 or the can electrode 36 will approximate LV impedance.

Figure 4:
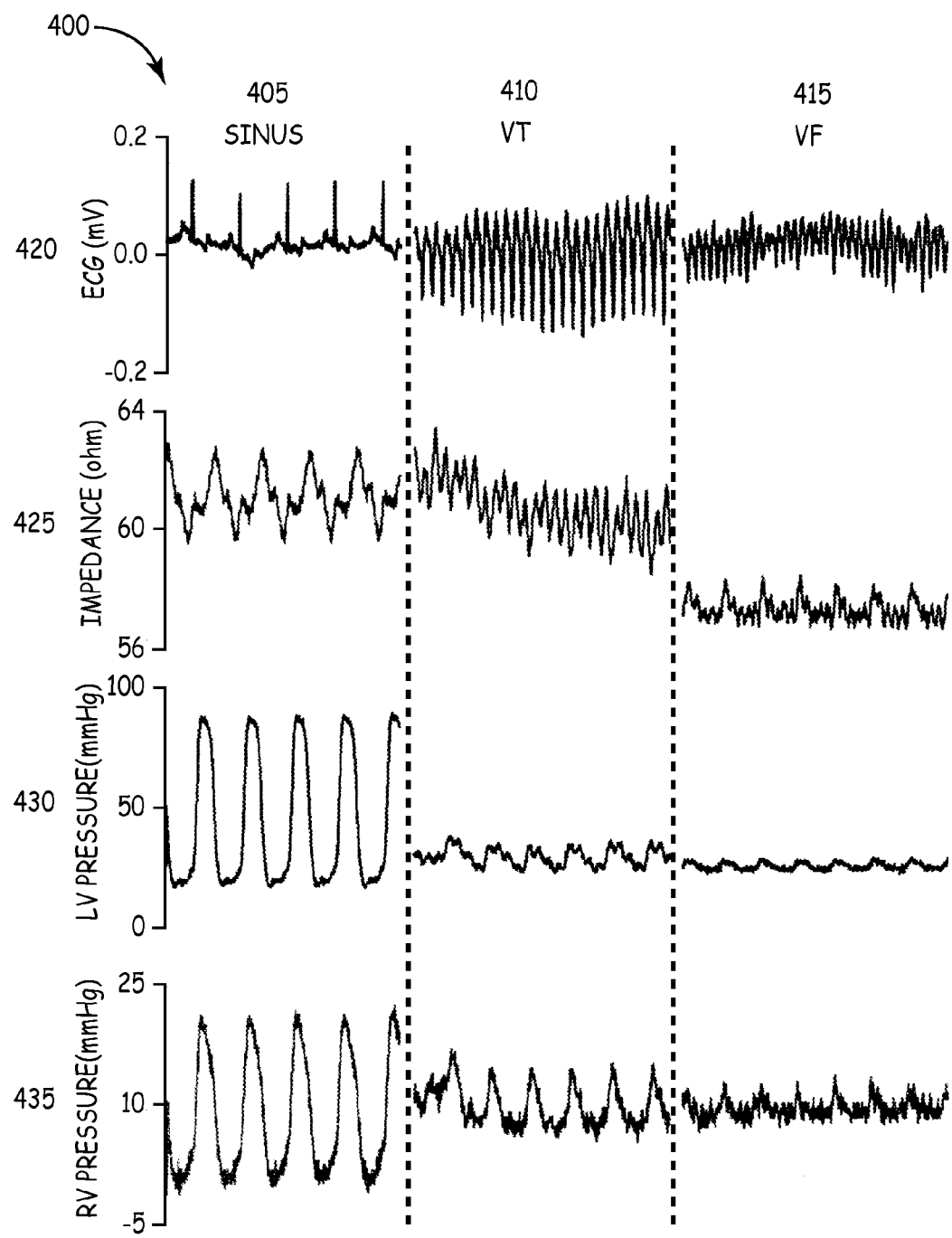
FIG. 4 is a collection of graphs illustrating various sensor data obtained during normal sinus rhythm (NSR), ventricular tachycardia (VT), and ventricular fibrillation (VF)

FIG. 4 is a graph 400 illustrating sampled data of various types and for various cardiac rhythms correlated together. As illustrated, for each type of data collected, the results for a sinus rhythm 405, VT 410, and VF 415 are illustrated. ECG (or EGM) data 420 illustrate a stable sinus rhythm 405 with discernable R waves. For VT 410, the ECG signal 410 illustrates signals of similar amplitude; however, due to the greatly increased rate the frequency is greater than that of the sinus rhythm 405. With VF 415, the signal 420 becomes irregular but still has a high frequency.

For the impedance values 425, the amplitudes of the waveforms tend to decrease, measured values decrease, and of course, frequency increases as the rhythms progress from sinus 405, to VT 410 and VF 415. For LV pressure 430 and RV pressure 435, there is also a notable decrease in amplitudes and an increase in frequency.

It will be appreciated that ex post facto analysis of these rhythms is deceptive. That is, to take idealized data during known rhythms for purposes of correlation and discussion tends to diminish the difficulty in processing these signals in real time. For example, on an analysis of ECG data 420 the distinction between sinus rhythm 405 and VT 410 may simply be rate, which as discussed above may be generally categorized but is often overlapping. The impedance values 425 illustrated tend to show a distinction between the rhythms; however, in a real world environment noise and other normal variation may obscure these differences; rendering both false positives and false negatives. Further, the amplitude changes may not be sufficiently discernable and the differences in actual measured values may be so patient specific as to make rhythm classification quite difficult. Similarly, with the pressure data 430, 435 there may be difficulty in establishing thresholds that reliably discriminate rhythms across patient populations. What this data set does illustrate is that the nature of the rhythm does have an effect on each of these parameters.

Figure 5A:
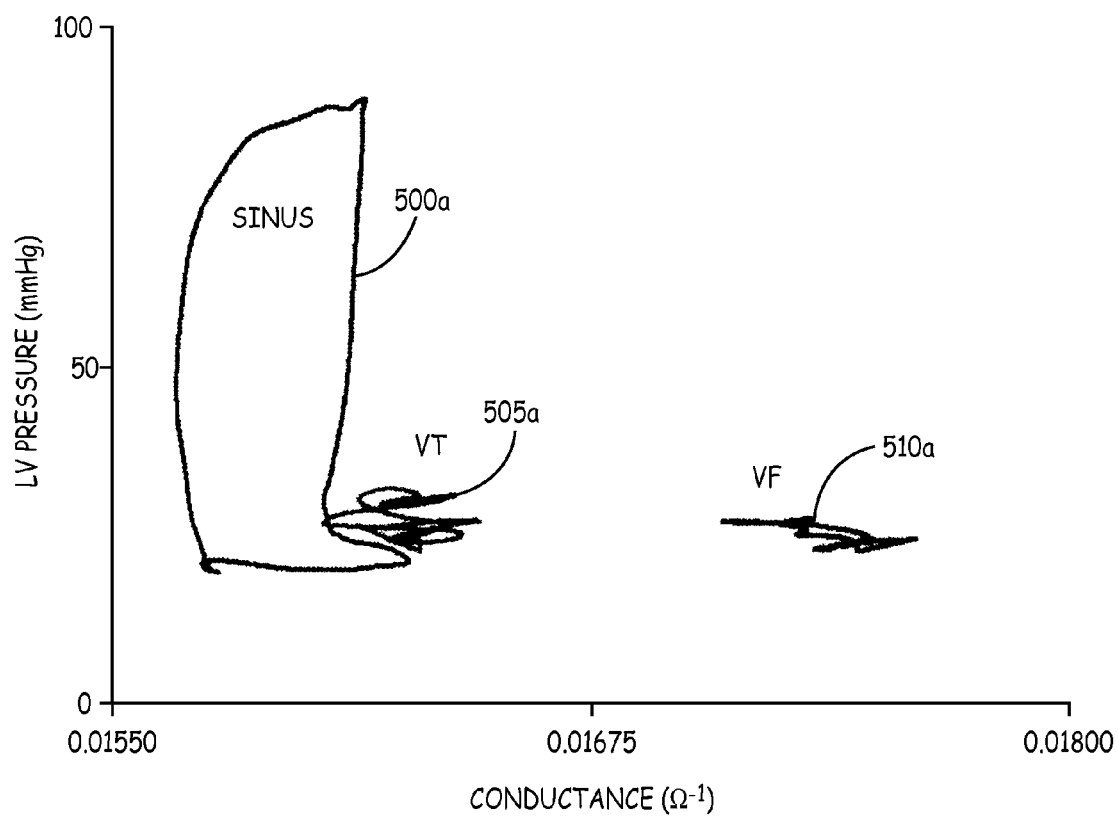
FIGS. 5A and 5B are phase loop plots of pressure and impedance data for NSR, VT, and VF events.
Figure 5B:
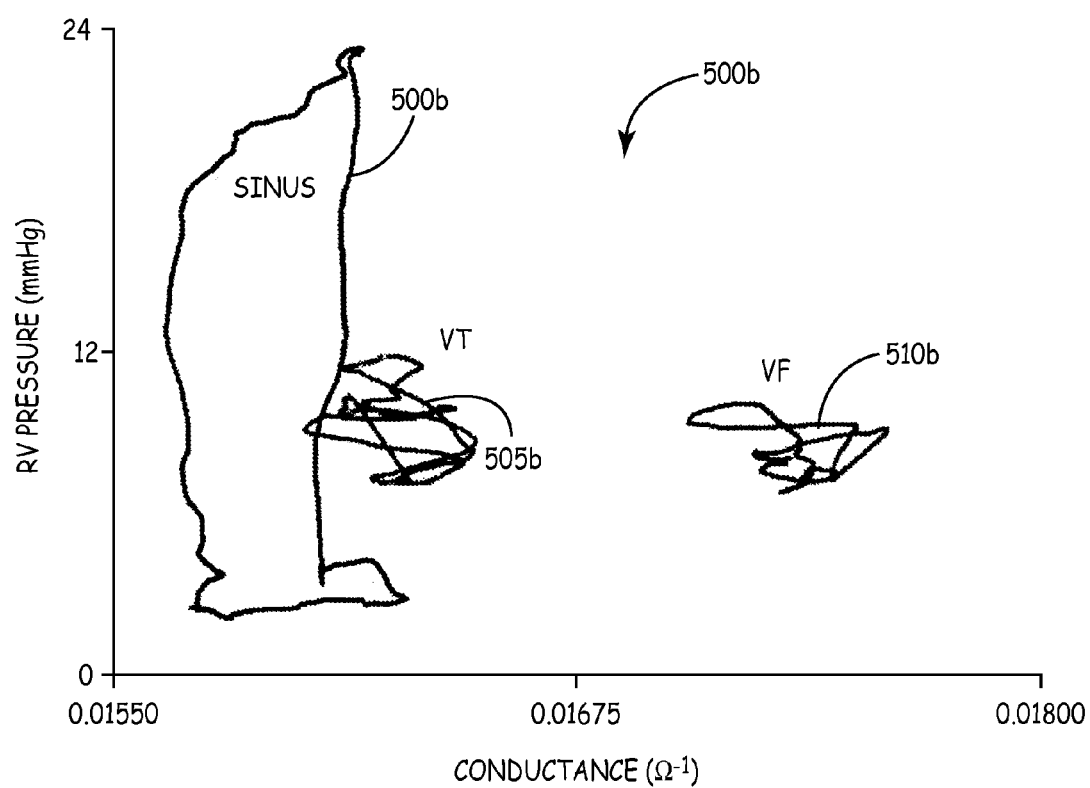

As previously stated, when in a normal sinus rhythm (NSR), cardiac pressure (more specifically ventricular pressure) is out of phase with (ventricular) impedance. This relationship is illustrated in the phase plots of FIGS. 5A and 5B. FIG. 5A is a phase plot based upon LV pressure data and FIG. 5B is a phase plot based upon RV pressure data. In both graphs, conductance (inverse of impedance) is plotted on the X axis while pressure is plotted on the Y axis. As illustrated, the out of phase relationship during NSR leads to a phase loop plot 500a, 500b that defines a substantial internal area. This indicates hemodynamic stability. That is, in efficient cardiac cycles changes in pressure inversely correlate to changes in the volume of the heart chamber (which correlated to impedance/conductance).

Conversely, in hemodynamically unstable rhythms blood flow (i.e., output) is reduced. For example, in VF the ventricle may be rapidly quivering which produces fluctuations in pressure. Without substantial cardiac output, the blood volume is not changing substantially despite these pressure variations; hence impedance changes will fail to correspond. In the phase plots of FIGS. 5A and 5B a hemodynamically unstable VT 505a, 505b and VF 510a, 510b are illustrated. As pressure and impedance are no longer out of phase, the resulting phase plot is chaotic and fails to define a substantive area.

Figure 6A:
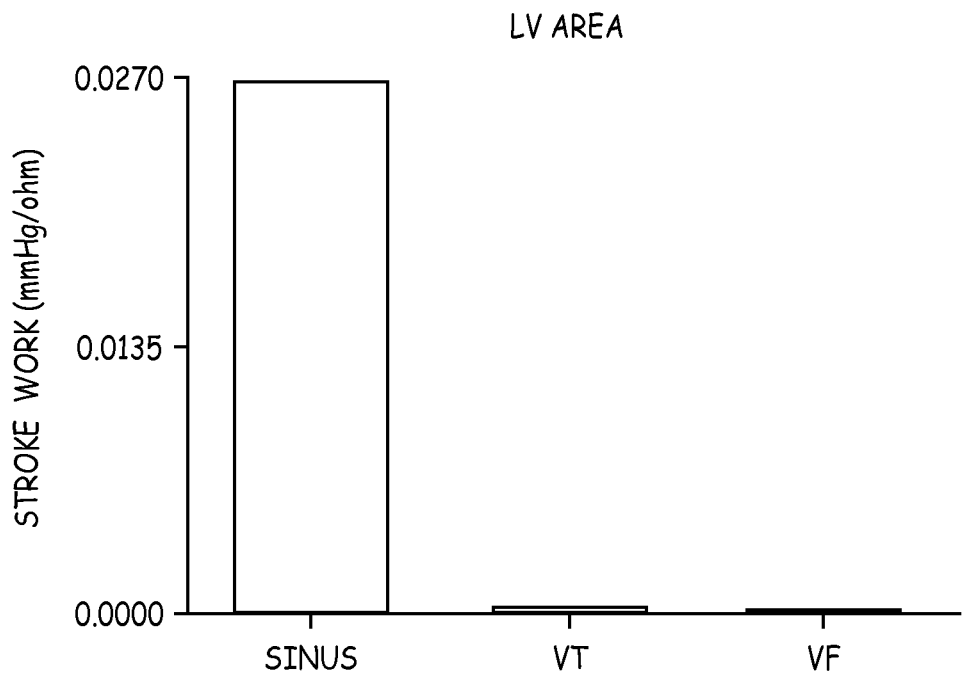
FIGS. 6A and 6B are graphs illustrating area calculations for the phase loop plots of FIGS. 5A and 5B.
Figure 6B:
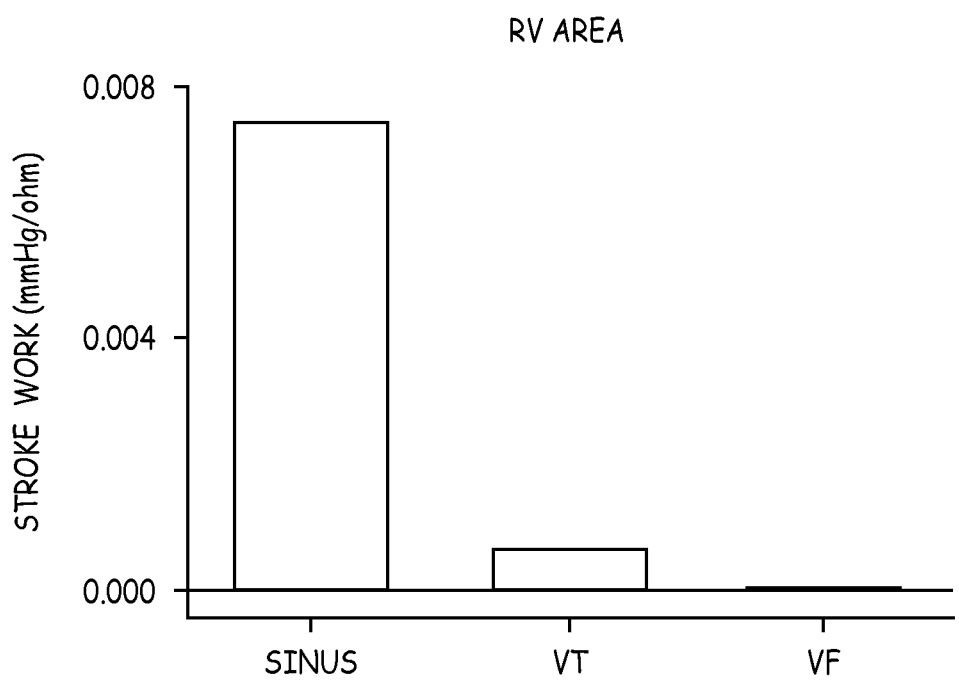

This result is further illustrated in the bar graphs of FIGS. 6A and 6B, which show the area defined by the phase plots of FIGS. 5A and 5B respectively. Area may be calculated using any of a variety of mathematical techniques, such as integrating an equation representing the phase plot. These graphs also define a parameter of stroke work, which corresponds to the integral of pressure with respect to volume (approximated as conductance). Stroke work approximates the work done by the ventricle to eject the stroke volume. Thus, higher stroke work corresponds with hemodynamic stability. As illustrated, the hemodynamically stable sinus rhythm has a significantly larger area as compared to the hemodynamically unstable VT and VF rhythms.

In practice, this classification would be utilized to determine whether particular therapy options were necessary or appropriate. In the illustrated examples, both the VT and VF episodes are hemodynamically unstable and a high power therapy (defibrillation) would be appropriate. In most instances, VF would be hemodynamically unstable and require such therapy. VT, on the other hand, while an arrhythmia may in fact be hemodynamically stable. That is, despite the high rate, cardiac output may be sufficient. Through not illustrated, if a VT were present and hemodynamically stable the proper phase relationship between pressure and impedance would be maintained and the phase loop diagram for this VT rhythm would more closely approximate that of NSR. In such a case, alternative therapy options become available and may be attempted for a longer period of time. For example, anti-tachy pacing (ATP) is a viable option. Further, because the current data monitors hemodynamic stability, ATP may be given a longer period of time before resorting to a more aggressive therapy. Spontaneous termination of the arrhythmia may also occur before the rhythm becomes unstable, thus eliminating the need for therapy.

Figure 7:
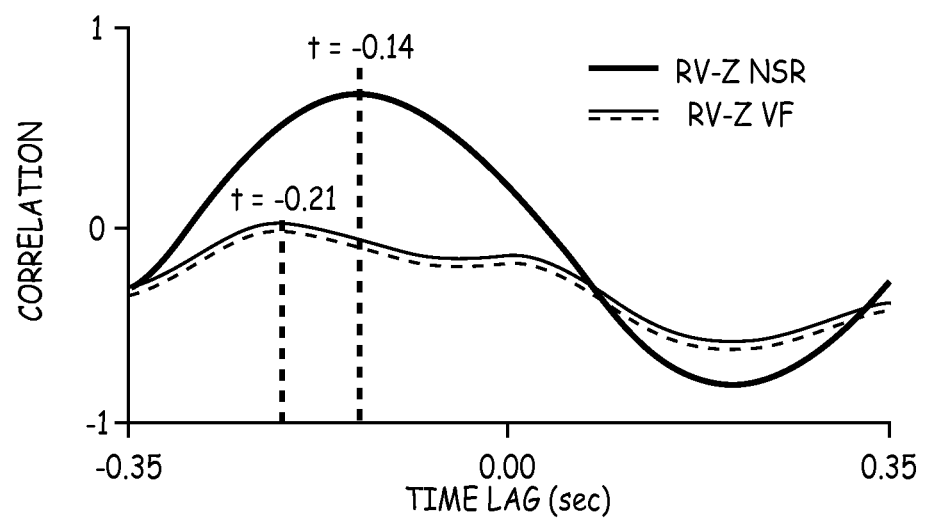
FIG. 7 is a cross correlation plot of impedance and pressure measurements.

FIG. 7 is another mechanism to illustrate the relationship between pressure and impedance. Specifically, FIG. 7 is a cross-correlation plot between right ventricular pressure and intrathoracic impedance during sinus rhythm (solid line) and VT/VT (solid/dashed line) derived from the same data used to produce the previous figures. As illustrated, VT/VF results in a dramatic shift in both the amplitude and time lag of the maximum correlation. These changes indicate a hemodynamically unstable arrhythmia.

Figure 8:
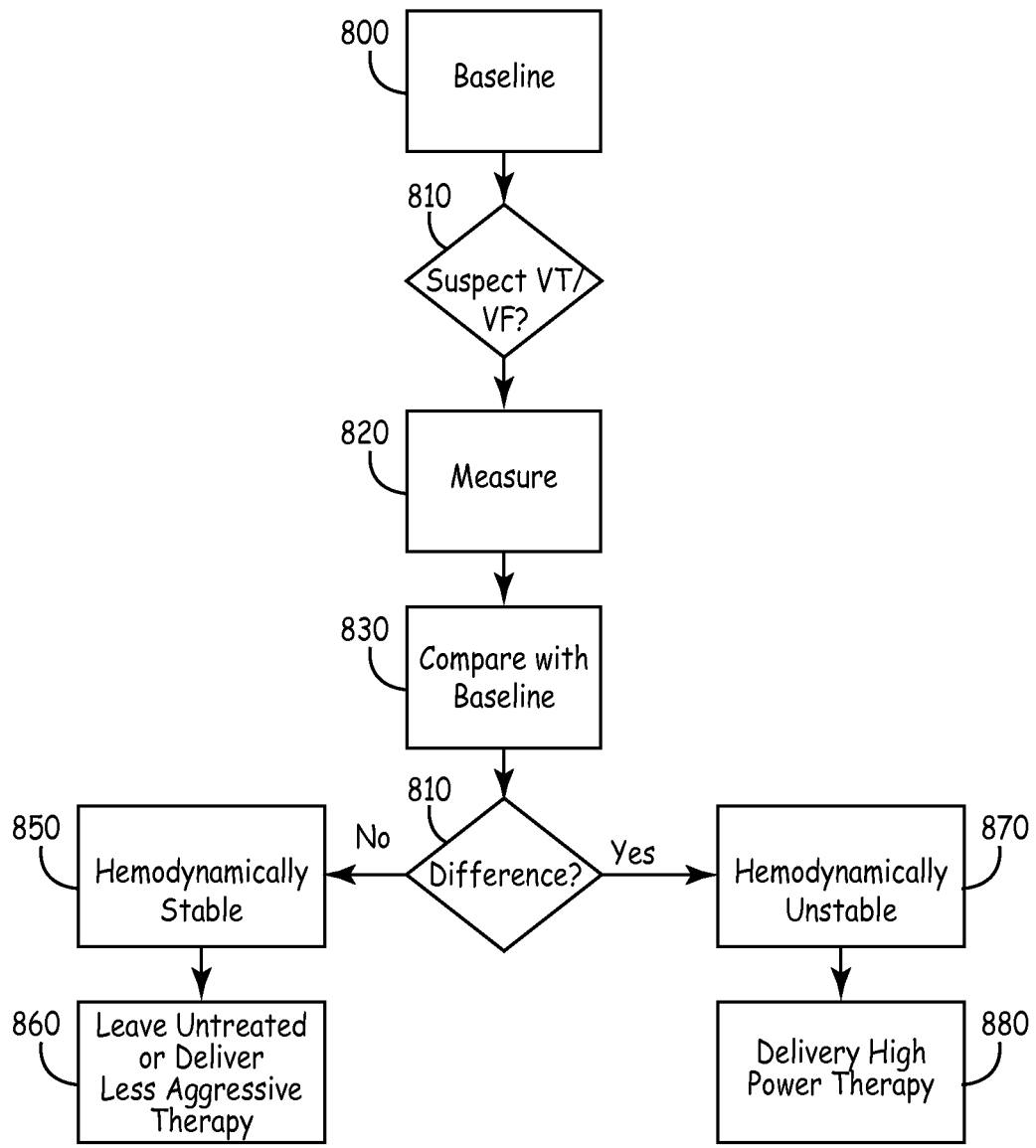
FIG. 8 is a flowchart describing an algorithm used in one embodiment of an IMD to determine hemodynamic stability based upon a phase relationship between pressure and impedance.

FIG. 8 is a flowchart describing a method of utilizing the phase relationship between pressure and impedance to determine hemodynamic stability in the selection and application of therapy. In this embodiment, a patient specific baseline is determined (800). A patient with an IMD 10 is monitored during a period of confirmed normal sinus rhythm (NSR). Pressure and impedance values are collected and correlated. It should be appreciated that in other embodiments, baseline data may be estimated from relevant patient populations.

The IMD 10 operates normally in accordance with known processing algorithms until VT/VF is suspected (810). This would most likely be based upon rate. At this point, pressure and impedance values are again measured (820), the phase relationship calculated, and the results are compared (830) with the previously established baseline to determine (840) if there is a difference. This may be done algorithmically by calculating an area defined by a phase plot between impedance/conductance measures verses pressure or plotting a cross-correlation between pressure and impedance. It should be appreciated that other mathematical or algorithmic techniques may be utilized to denote and quantify the phase relationship between pressure and impedance will remaining within the spirit and scope of the present disclosure.

If there is no difference or the difference is less than a threshold, the IMD 10 determines (850) that the rhythm is hemodynamically stable (850). In this instance, the IMD 10 may (depending upon the other parameters of the rhythm)

leave the rhythm untreated or deliver therapies that are less aggressive than defibrillation (such as ATP).

If the comparison between the current pressure/impedance data indicates a large difference (840), then the IMD 10 determines (870) that the rhythm is hemodynamically unstable and that high power therapy (defibrillation) is warranted (880).

The particular thresholds set may be based upon patient population data or set to patient specific parameters. Referring to FIGS. 5A, 5B, 6A, and 6B there is a clear distinction between hemodynamically stable and unstable rhythms. In one embodiment, the threshold is set to a particular percentage of the baseline NSR area taken from the phase plots. Thus, if the measured values fall below X percent of baseline, the rhythm is declared unstable. For example, in one embodiment if the measured data is less than 50% of the baseline, the rhythm is declared unstable. In another embodiment, if the measured data is less than 10% of the baseline, the rhythm is declared unstable.

As described, the IMD 10 relies upon other parameters (e.g., rate) to trigger a suspected VT/VF (810), at which point, impedance and pressure are measured (820) and compared (830) with a baseline. It should be appreciated that in an alternative embodiment, impedance and pressure are measured continuously or at a high frequency and either continuously (or frequently) compared with the baseline. In this manner, the phase relationship between pressure and impedance would be useful to initially indicate a hemodynamically unstable rhythm, rather than to just confirm the same. Further, when used in this manner, the phase relationship may identify a declining cardiac rhythm and permit less aggressive therapy prior to reaching hemodynamic instability.

As described, various embodiments utilize a phase relationship between sensed pressure and impedance data to determine the hemodynamic stability of a given cardiac rhythm. This determination is then utilized to select an appropriate therapy.

Techniques and technologies described herein in terms of functional and/or logical block components and various processing steps. It should be appreciated that such block components may be realized by any number of hardware, software, and/or firmware components configured to perform the specified functions. For example, an embodiment of a system or a component may employ various/s integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments may be practiced in conjunction with any number of IMD configurations, medical device therapies, and monitoring/diagnostic equipment, and that the system described herein is merely one suitable example.

For the sake of brevity, conventional techniques related to signal sensing and signal processing, and other functional aspects of the systems (and the individual operating components of the systems) may not have been described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the subject matter.

The system embodiments may be described herein with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits.

When implemented in software or firmware, various elements of the systems described herein (which may reside at an IMD, an external monitor device, or elsewhere in the system environment) are essentially the code segments or instructions that perform the various tasks. The program or code segments can be stored in a processor-readable medium or transmitted by a computer data signal embodied in a carrier wave over a transmission medium or communication path. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

What is claimed is:

1. A method comprising:
   obtaining cardiac pressure data;
   obtaining cardiac impedance data;
   correlating the cardiac pressure data and cardiac impedance data to determine a phase relationship between the cardiac pressure data and the cardiac impedance data; and
   determining a degree of hemodynamic instability of a cardiac rhythm during an arrhythmia based upon the determined phase relationship.

2. The method of claim 1, wherein the hemodynamic status is determined to be stable when the cardiac pressure data is out of phase with the cardiac impedance data.

3. The method of claim 1, wherein correlating the cardiac pressure data and cardiac impedance data further includes generating a phase plot between the cardiac pressure data and the cardiac impedance data.

4. The method of claim 3, further comprising determining an area defined by the phase plot wherein the determined area is utilized to determine the hemodynamic status.

5. The method of claim 4, further comprising determining a baseline value of the phase relationship during normal sinus rhythm.

6. The method of claim 5, further comprising wherein the determined area is compared to the baseline value to determine the hemodynamic status.

7. The method of claim 1, wherein correlating the cardiac pressure data and the cardiac impedance data further comprises generating a cross correlation plot of the cardiac impedance data with the cardiac pressure data.

8. The method of claim 1, further comprising selecting a cardiac therapy based upon the determined hemodynamic status.

9. The method of claim 8, wherein a defibrillation therapy is only selected if the hemodynamic status is determined to be unstable.

10. A method of operating an implantable medical device comprising:
sensing cardiac pressure to obtain cardiac pressure data;
sensing cardiac impedance to obtain cardiac impedance data;
determining a phase relationship between the cardiac pressure data and the cardiac impedance data; and
classifying a degree of hemodynamic instability of an arrhythmia based upon the determined phase relationship.

11. The method of claim 10, further comprising:
determining a baseline value during normal sinus rhythm;
comparing the determined phase relationship to the baseline value in classifying the hemodynamic status.

12. The method of claim 11, wherein determining the phase relationship includes generating a phase loop plot and determining an area of the phase loop plot.

13. The method of claim 12, further comprising comparing the area of the phase loop plot to a baseline area and determining a difference, wherein the difference is indicative of the hemodynamic status.

14. The method of claim 11, further comprising identifying a suspected arrhythmia, wherein identification of the suspected arrhythmia triggers the steps of sensing the cardiac pressure and impedance data and the step of determining the phase relationship.

15. The method of claim 14, further comprising selecting a cardiac therapy based upon the classification of the hemodynamic status.

16. The method of claim 14, wherein defibrillation is only selected as the cardiac therapy if the hemodynamic status indicates that the arrhythmia is hemodynamically unstable.

17. A method of operating an implantable medical device (IMD) comprising:
sensing cardiac pressure;
sensing cardiac impedance; and
determining a degree of hemodynamic instability during an arrhythmia based upon a phase relationship between the sensed cardiac pressure and the sensed cardiac impedance.

18. The method of claim 17, wherein delivering therapy comprises only delivering a defibrillation waveform if the cardiac rhythm is hemodynamically unstable.

19. The method of claim 17, further comprising generating a phase plot between the sensed pressure and sensed impedance and determining a phase plot area.

20. The method of claim 19, further comprising comparing the phase plot area to a baseline phase plot area to determine hemodynamic stability.

21. A method comprising:
obtaining cardiac pressure data;
obtaining cardiac impedance data;
correlating the cardiac pressure data and cardiac impedance data to determine a phase relationship between the cardiac pressure data and the cardiac impedance data;
determining a hemodynamic stability of a cardiac rhythm based upon the determined phase relationship; and
determining a patient-specific baseline by correlating the pressure data and impedance data during a period of confirmed normal sinus rhythm, wherein determining the patient-specific baseline comprises calculating an area defined by a phase plot between the pressure data and the impedance data,
wherein determining the hemodynamic stability comprises calculating a next area defined by a phase plot between the pressure data and the impedance data measured during a suspected tachyarrhythmia and comparing the next area to the baseline.

* * * * *